US006536429B1

United States Patent
Pavlov et al.

(10) Patent No.: US 6,536,429 B1
(45) Date of Patent: *Mar. 25, 2003

(54) METHOD OF PRODUCING A BREATHING MIXTURE AND AN APPARATUS FOR APPLYING THE METHOD

(76) Inventors: Boris Nikolaevich Pavlov, Russian Federation, Moscow 113545, ul. Podolskikh kursantov, d korp. 2, kv.1 (RU); Alexei Timofeevich Logunov, Russian Federation, Moskovskaya obl., 141700, Dolgoprudny (RU); Igor Alexeevich Smirnov, Russian Federation, Moscow 123480, ul. Turistskaya, d. 18, kv.2 (RU); Viktor Mikhailovich Baranov, Russian Federation, Moscow 123182, ul. Aviatsionnaya, d. 13, kv. (RU); Georgy Ivanovich Lastochkin, Russian Federation, Leningradskaya obl., 189510 Lomonosov, Morskoi pr., d. 10, kv. 7.1 (RU); Alexandr Nikolaevich Kotov, Russian Federation, 125057 Moscow, ul. Novopeschanaya, d. 6, kv. 5 (RU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,609
(22) PCT Filed: Sep. 19, 1996
(86) PCT No.: PCT/RU96/00270
§ 371 (c)(1),
(2), (4) Date: Mar. 20, 1998
(87) PCT Pub. No.: WO97/10869
PCT Pub. Date: Mar. 27, 1997

(30) Foreign Application Priority Data

Sep. 20, 1995 (RU) .............................. 95116346

(51) Int. Cl.[7] .................. A61M 16/00; F23D 11/00; F23D 14/00

(52) U.S. Cl. .................. 128/203.26; 128/203.12; 128/203.16; 128/205.11; 128/205.13; 128/205.28; 128/914

(58) Field of Search ................ 128/200.19, 200.21, 128/200.22, 203.12, 203.16, 203.17, 203.22, 203.25, 203.26, 203.27, 203.28, 203.29, 205.11, 205.13, 205.14, 205.28, 205.17, 914, 205.24, 204.17

(56) References Cited

U.S. PATENT DOCUMENTS 4,127,121 A * 11/1978 Westenskow et al. .. 128/203.28

(List continued on next page.)

FOREIGN PATENT DOCUMENTS

EP    A1 0425092    5/1991

(List continued on next page.)

*Primary Examiner*—Aaron J. Lewis
*Assistant Examiner*—Joseph F. Weiss, Jr
(74) *Attorney, Agent, or Firm*—J. Herbert O'Toole; Nexsen Pruet Jacobs & Pollard, LLC

(57) ABSTRACT

The gas mixture is fed in a circulating stream at a volume flow rate of 3–120 l/min, the mixture being cleaned and its temperature and qualitative and quantitative composition regulated. The gas mixture contains oxygen and at least one of the following gases in quantities of up to 95%: helium, argon, neon, krypton, xenon, radon, nitrogen, nitrous oxide, sulfur hexafluoride, or a mixture of these gases. Pharmaceutical preparations can also be introduced into the breathing mixture, and the level of inhaled carbon dioxide can be adjusted with the aid of the exhaled carbon dioxide. The apparatus has a circulation loop comprising connecting pipes, a respirator bag, flow booster, temperature regulator, and at least one absorption unit for absorbing the carbon dioxide, moisture, and harmful trace contamination exhaled by the patient. The circulation loop is connected to the oxygen gas analyzer and is also provided with a carbon dioxide gas analyzer and temperature gauge; the latter two elements, together with the oxygen gas analyzer, form a measurement unit that is electrically connected to the control unit. The mask is connected to the loop by a tube with valves.

5 Claims, 1 Drawing Sheet

U.S. PATENT DOCUMENTS

| | | | | |
|---|---|---|---|---|
| 4,204,536 A | * | 5/1980 | Albarda | 128/204.22 |
| 4,572,208 A | * | 2/1986 | Cutler et al. | 600/532 |
| 4,596,246 A | * | 6/1986 | Lyall | 128/202.27 |
| 4,611,590 A | * | 9/1986 | Ryschka et al. | 128/203.14 |
| 4,791,922 A | * | 12/1988 | Lindsay-Scott et al. | 128/205.28 |
| 4,883,051 A | * | 11/1989 | Westenskow et al. | 128/204.21 |
| 4,903,693 A | * | 2/1990 | Yasue | 128/203.12 |
| 4,909,246 A | * | 3/1990 | Kiske et al. | 128/205.14 |
| 4,938,210 A | * | 7/1990 | Shene | 128/203.12 |
| 4,986,268 A | * | 1/1991 | Tehrani | 128/204.22 |
| 4,991,576 A | * | 2/1991 | Henkin et al. | 128/203.28 |
| 5,024,219 A |   | 6/1991 | Dietz | |
| 5,087,597 A | * | 2/1992 | Leal et al. | 502/62 |
| 5,165,392 A | * | 11/1992 | Small, Jr. | 128/200.18 |
| 5,178,138 A | * | 1/1993 | Walstrom et al. | 128/200.23 |
| 5,423,313 A | * | 6/1995 | Olsson et al. | 128/204.21 |
| 5,429,123 A | * | 7/1995 | Shaffer et al. | 128/204.23 |
| 5,485,827 A | * | 1/1996 | Zapol et al. | 128/200.14 |
| 5,490,499 A | * | 2/1996 | Heinonen et al. | 128/203.28 |
| 5,509,406 A | * | 4/1996 | Kock et al. | 128/203.14 |
| 5,537,992 A | * | 7/1996 | Bjoernstijerna et al. | 128/203.14 |

FOREIGN PATENT DOCUMENTS

| | | |
|---|---|---|
| RU | 1793934 | 2/1993 |
| RU | C1 2004261 | 12/1993 |
| SU | A1 1304821 | 4/1987 |
| SU | A 1335294 | 9/1987 |

* cited by examiner

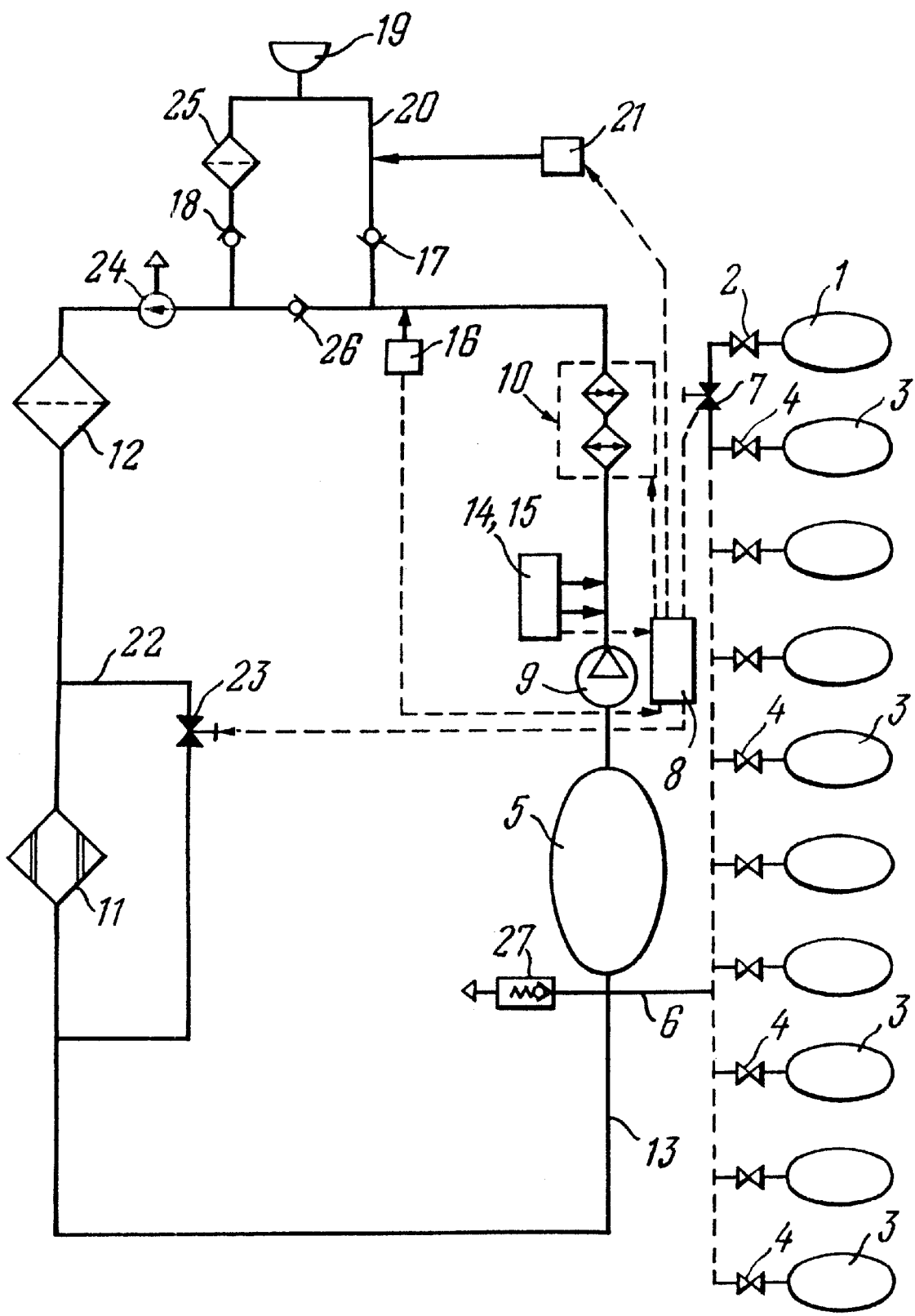

METHOD OF PRODUCING A BREATHING MIXTURE AND AN APPARATUS FOR APPLYING THE METHOD

TECHNICAL FIELD

The invention relates to medicine and means of medical engineering; it can find application in treating a number of diseases with the aid of breathing gas mixtures, including affections resulting from emergency situations.

BACKGROUND ART

One prior-art method for producing a gas mixture for intermittent normobaric hypoxia is known to comprise depleting atmospheric air of oxygen by compressing it in a compressor up to 0.3 to 1.5 MPa and passing the thus-compressed air through a polymer membrane made of hollow fibres, followed by feeding the resultant mixture to the patient through a-flow rate meter, a humidifier, and a mask provided with a breathing valve, and a device for carrying said method into effect, comprising a breathing bag, a mask with a breathing valve, to which mask the prepared gas mixture is fed along pipings, a compressor, a polymer membrane, a humidifier, a flow rate meter, and a gas analyzer (RU 2,004,261, A2 1994, IPC A61M 16/00).

The closest to the method proposed in the present invention is the method for forming a breathing gas mixture by mixing compressed gases fed along a piping, followed by controlled feeding of said gas mixture to the breathing mask, and an apparatus which realizes said method, comprising- a device for producing a gas mixture, having a source of compressed gas, said source communicating therewith through a gas mixture composition regulator and a flow rate meter, a breathing bag, a breathing mask with an inhalation valve and an exhalation valve, an oxygen gas analyzer, and a control unit (SU 1,793,934, A2, 1993, A61M 16/00).

However, field of application of said known methods, apparatus, and devices in medical practice is limited due to an insufficient therapeutic efficacy stemming from the fact that they use an atmospheric air (nitrogen-oxygen) mixture as the breathing mixture.

DISCLOSURE OF THE INVENTION

The present invention has for its principal object to extend the functional capabilities and increase the efficiency of treatment by modifying a qualitative composition of inhaled gas mixtures, as well as to reduce the consumption of gases constituting said mixtures.

The foregoing object is accomplished in a method for forming a breathing gas mixture, comprising feeding said mixture in a circulatory flow at a volume rate of flow from 3 to 120 l/min and cleaning it of carbon dioxide, moisture, and harmful microimpurities; the temperature of the gas mixture when inhaled is controlled in a range of from minus 10 to plus 130° C.; there are also fed to said mask binary and multicomponent gas mixtures of the various qualitative and quantitative composition, said gas mixtures containing oxygen and at least one of the following gases (with a maximum 95% percent content of each gas in the mixture involved): helium, and/or argon, and/or neon, and/or krypton, and/or xenon, and/or radon, and/or nitrogen, and/or nitrous oxide, and/or sulfur hexafluoride, or a mixture thereof; the breathing mixture may be doped with medicinal agents; the carbon-dioxide content of the inhaled air may be adjusted in a range from 0.0001 to 5%, using the exhaled carbon dioxide for the purpose; inhalation resistance may be reduced by admitting an excess pressure; the carbon-dioxide absorption conditions may be improved by increasing the rate of gas mixture flow through a sorbent bed, and the carbon-dioxide content of the inhaled gas mixture may be adjusted by bifurcating the exhaled gas mixture flow into two streams one of which is admitted to pass through the sorbent bed, while the other stream bypasses the latter.

The foregoing object is also accomplished in an apparatus for forming a breathing gas mixture, comprising a device for producing a gas mixture, said device appearing as a number of containers holding compressed oxygen and also at least one of the following gases: helium, and/or argon, and/or neon, and/or krypton, and/or xenon, and/or radon, and/or nitrogen, and/or nitrous oxide, and/or sulfur hexafluoride, or a mixture thereof, said containers communicating with a breathing bag through pipings provided with stop valves, at least the compressed oxygen container being provided with a valve remote-controlled from the control unit; the apparatus is provided with a circulation circuit built up by the breathing bag, a gas flow inducer, a temperature controller, and at least one absorbent filter of carbon dioxide, moisture, and harmful microimpurities exhaled by the patient into the apparatus, all these intercommunicating through pipings; said circulation circuit communicates with an oxygen gas analyzer and is additionally provided with a carbon-dioxide gas analyzer and a temperature gauge, both of which establish, together with said oxygen analyzer, a measuring unit electrically connected to the control unit, and the mask is connected, through pipings with valves, to said circulation circuit; an inhaler may be interposed between the inhalation valve and the mask and be connected to the piping that feeds the gas mixture to the mask, said inhaler being aimed at feeding medicinal agents or moisture; the carbon-dioxide absorbent filter may be by-passed by an additional piping provided with stop valves and aimed at feeding part of a carbon dioxide-enriched gas flow directly to the breathing bag, thus by-passing said carbon-dioxide absorbent filter; an exhalation piping may be provided with a gas flow switch in order that the apparatus may operate on an open cycle; the sorbent may be re-vivifiable and be provided with a thermal reactivator; the apparatus may further comprise a device for cleaning gases of microflora, said device being cut into the gas-mixture exhalation piping; the circulation circuit may comprise a non-return valve preventing reversal of the gas flow; the apparatus may further comprise a device for determining patient's basal metabolism against his/her breathing, and the breathing bag may be provided with a relief valve with an adjustable pressure setting.

The herein-proposed method for producing a breathing gas mixture contemplates use of rather costly gases, especially helium, whereas performing circulation jointly with regeneration of a predetermined mixture with the aid of the proposed apparatus is most economic and efficient as minimizing loss of the gases used.

Practical utilization of the present invention enables one to obtain a technical effect consisting in that use of gases having properties other than air has contributes to a high therapeutic effect, while feeding gases in a circulation flow and their regeneration allows of using the gas mixture both efficiently and economically, and the use of the invention becomes more efficient due to the fact that the temperature of the breathing mixture is controlled and inhalation of medicinal agents is provided.

Furthermore, a possibility of using a variety of gases in the breathing mixture allows of rendering medical aid to patients who sustained overcooling, this being due to extrahigh heat conductivity of helium. On the other hand, use of, e.g., nitrous oxide enables one to relieve pain in wounded patients, as well as to use the apparatus as the anesthesia apparatus in surgery.

BRIEF DESCRIPTION OF THE ACCOMPANYING DRAWINGS

In what follows the present invention is illustrated in the accompanying drawing, presenting a functional diagram of the apparatus for forming a breathing mixture, whereby the herein-proposed method is carried into effect.

BEST METHOD OF CARRYING OUT THE INVENTION

The apparatus comprises a device for forming a gas mixture, said device appearing as a container 1 holding compressed oxygen (O2) and provided with a control valve 2, as well as at least one container 3 provided with a control valve 4 and holding one of the following gases: helium (He) nitrous oxide (N20), sulfur hexafluoride (SF6), as well as other gases (namely, Rn, Xe, Kr, Ar, Ne, N2) or mixtures thereof. The containers 1 and 3 communicate with a breathing bag 5 through pipings 6. The container 1 holding O2 has a controllable valve 7 connected to a control unit 8. The apparatus further comprises a gas flow inducer 9, a temperature controller 10, absorbent filters 11 and 12 of carbon dioxide, and moisture and harmful impurities, respectively, exhaled by the patient into the apparatus, said absorbent filters communicating to each other and to the breathing bag through a piping so as to establish a closed circulation circuit, which is also provided with an oxygen gas analyzer 14 and a carbon-dioxide gas analyzer 15, and a temperature gauge 16, all of these forming a unit for measuring the gas mixture parameters, electrically connected to the control unit 8. A mask 19 is connected to the circulation circuit along a piping 20 and through an inhalation valve 17 and an exhalation valve 18. An inhaler 21 connected to the control unit 8 may be cut into the piping 20 between the inhalation valve 17 and the mask 20 for feeding medicinal agents or moisture. The carbon-dioxide absorbent filter 11 may be provided with a by-pass piping 22 having a controllable valve 23 connected to the control unit 8 for feeding part of a carbon dioxide-enriched gas flow directly to the breathing bag 5, thus by-passing the absorbent filter 11. A gas flow switch 24 may be provided in the exhalation line of the circulation circuit in order that the apparatus may operate on an open cycle, as well as a device 25 for cleaning gases of microflora. The circulation circuit of the apparatus may further comprise a non-return valve 26 aimed at providing a required direction of the gas flow in the circulation circuit (i.e., through the absorbent filters 12 and 11) and preventing filling the breathing bag 5 with an unfiltered gas mixture, that is, preventing reversal of the gas flow.

The breathing bag 5 may further comprise a relief valve 27 with an adjustable pressure setting, which protects the breathing bag against bursting with compressed gases by appropriately adjusting the bag interior pressure.

The absorbent filter 11 may be revivifiable and be provided, e.g., with a thermal reactivator.

Carbon dioxide is absorbed when a humid gas mixture passes through the absorbent filter 11, according to the following reaction:

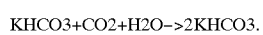

Heating the absorbent filter 11 to 220–240° C. results in that the reverse reaction proceeds:

which is accompanied by releasing carbon-dioxide gas and moisture into the surrounding atmosphere, as well as by restoring the absorptive capacity of the sorbent, whereby the thermally reactivated a 11 can be reused many times.

In the alternative embodiments of the proposed apparatus use may be made of a sorbent having some other chemical composition, (solid, such as zeolites, or liquid, such as amines) buy being obligatorily a revivifiable one.

It is due to extremely high fluidity and thermal conductivity of helium that favorable conditions are provided for heating human organism, as well as for facilitating pulmonary ventilation. Moreover, while varying the oxygen content of the breathing mixture treatment under conditions of hyperoxia, normoxia, and hypoxia can be performed.

The flow inducer 9 is instrumental, whenever necessary, in reducing gasodynamic inhalation resistance by admitting an excess pressure, which is especially important in case of a severe patient's condition accompanied by stertorous respiration.

Provision is also made in the proposed apparatus for establishing hypercapnic conditions due to a controlled bifurcating of the exhaled gas flow into two parts, one of which is directed to the carbon-dioxide absorbent filter 11, while the other bypasses said filter. Whenever the whole gas flow passes through the carbon-dioxide absorbent filter 11, the carbon-dioxide concentration in the inspired air approximates zero. In addition, a possibility is provided of administering pharmaceuticals which can be fed through the inhaler 21 to the piping 20 between the inhalation valve 17 and the mask 19.

The exhaled air enriched with carbon dioxide, moisture, harmful impurities, and microflora first is passed through the device 25 for cleaning air of microflora, and then is fed through the exhalation valve 18 to the carbon-dioxide absorbent filter 11 which is provided with a bypass pipeline having the controllable valve for adjusting the carbon-dioxide content of the inhaled air in a range from 0.0001 to 5%, whereupon the gas mixture is fed, through the breathing bag 5 and the flow inducer 9, to the oxygen gas analyzer 14. Use of such gas mixtures (with an increased carbon-dioxide content, the so-called hypercapnic mixtures) permits, e.g., improving oxygen supply of cerebral blood vessels.

Owing to the fact that helium is in substantially inassimilable in human organism and oxygen consumption rate is within 7 and 200 l/min (depending on physical load, general state of organism, and other factors), the oxygen gas analyzer 14 may indicate that the O2 content of the gas mixture is below the preset value. As a result, a signal is delivered through the control unit 8 to the controllable valve 7 to open for a metered oxygen supply to the circulation circuit. Once the oxygen concentration therein has reached the preset value, the controllable valve 7 is closed. The volume rate of the gas mixture flow along a closed circuit is from 3 to 120 l/min in accordance with patient's demand.

INDUSTRIAL APPLICABILITY

The invention can find application in medical practice in treating a number of diseases and in rendering an efficient medical aid to patients, victims of emergency situations, and sufferers of home accidents.

What is claimed is:
1. An apparatus for providing a breathing gas mixture to a patient, comprising:

a closed loop gas circulation circuit including in series
- a breathing bag (5),
- a gas flow inducer (9),
- a temperature controller (10),
- an inhalation valve (17),
- a medicine inhaler (21),
- a patient mask (19),
- a device (25) for cleaning gas of microflora,
- an exhalation valve (18),
- a first carbon dioxide absorbent filter (12),
- a second carbon dioxide absorbent filter (11), sources of compressed gases including oxygen (1) and at least one gas selected from the group consisting of the gases (3) helium, argon, neon, krypton, xenon, radon, nitrogen, nitrogen monoxide and sulfur hexafluoride, piping (6) connecting said sources of gases to said breathing bag (5), an oxygen control valve (7) controlling flow in said piping (6) from only said oxygen (1), a control valve (4) in said piping controlling flow from each gas of said group of gases, a bypass pipe (22) connected to said circulation circuit in bypassing relation to one of said carbon dioxide absorbent filters, a bypass control valve (23) in said bypass pipe (22) for controlling flow in said bypass pipe (22), a control unit (8) connected in controlling relation to said oxygen control valve (7) and to said bypass control value (23)

a temperature sensor (18) sensing temperature of gases in said circuit delivered to said inhaler valve (17), said temperature sensor (18) being connected in data delivery relation to said control unit (8), said control unit (8) adjusting said temperature controller (10) to provide a gas mixture at a temperature within a predetermined temperature range, an oxygen gas analyzer (14) connected to said circuit between said breathing bag (5) and said inhalation valve (17) and connected in data delivery relation to said control unit (8), a carbon dioxide gas analyzer (15) connected to said circuit between said breathing bag (5) and said inhalation valve (17) and connected in data delivery relation to said control unit (8), and said control unit (8) automatically adjusting said oxygen control valve (7) to vary the flow of oxygen (1) to said breathing bag (5) in response to data received from said (22) analyzer (14) and said control unit (8) automatically adjusting said bypass control valve (23) in response to data received from said carbon dioxide gas analyses (15).

2. The apparatus as set forth in claim 1 wherein said breathing bag is provided with a relief valve having an adjustable pressure setting.

3. The apparatus as set forth in claim 1 wherein said one carbon dioxide absorbent filter is provided with a thermal regenerator.

4. The apparatus as set forth in claim 1 and further comprising a medical agent inhaler (21) connected to said circuit between said inhaler valve (17) and said patent mask (19).

5. A method for providing a breathing gas mixture to a patient comprising the steps of:

providing a closed loop circuit for said breathing gas mixture including a breathing bag (5), a patient breathing mask (19), a first carbon dioxide absorbent filter (11) and a second carbon dioxide absorbent filter, supplying said breathing bag with a gas mixture including oxygen and at least one gas from a group of gases including helium, argon, neon, krypton, xenon, radon, nitrogen, nitrous oxide and sulfur hex fluoride and providing a control system which
- regulates the flow of said breathing gas between 3 and 120 l/minute,
- adjusts the temperature of said breathing gas between minus 11 and plus 130 degrees Celsius and
- regulates oxygen content in said gas mixture in response to analysis of oxygen content in gas mixture supplied to said breathing mask and
- bypasses one of said carbon dioxide absorbent filters in response to the carbon dioxide content in said gas mixture delivered to said breathing mask (19) falling below a predetermined level.

* * * * *

UNITED STATES PATENT AND TRADEMARK OFFICE
CERTIFICATE OF CORRECTION

PATENT NO.     : 6,536,429 B1
DATED          : March 25, 2003
INVENTOR(S)    : Pavlov et al.

It is certified that error appears in the above-identified patent and that said Letters Patent is hereby corrected as shown below:

<u>Title page,</u>
Item [73], should be
-- Panina, Elena Vladimoirovna
   UL. B. Bronnaya D. 19, KV.8
   Moskow, 103104, Russian Federation --

Signed and Sealed this

Twenty-fifth Day of November, 2003

JAMES E. ROGAN
*Director of the United States Patent and Trademark Office*